US008293755B2

(12) United States Patent
Linnane

(10) Patent No.: US 8,293,755 B2
(45) Date of Patent: *Oct. 23, 2012

(54) TREATMENT OF STATIN SIDE EFFECTS USING URIDINE DERIVATIVES

(75) Inventor: Anthony William Linnane, Canterbury (AU)

(73) Assignee: Magral Pty Ltd., Richmond, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/692,045

(22) Filed: Jan. 22, 2010

(65) Prior Publication Data
US 2010/0184717 A1 Jul. 22, 2010

Related U.S. Application Data

(63) Continuation of application No. 10/499,078, filed as application No. PCT/AU02/01685 on Dec. 13, 2002, now abandoned.

(30) Foreign Application Priority Data

Dec. 13, 2001 (AU) ................................ PR9511/01

(51) Int. Cl.
*A61K 31/513* (2006.01)
*A61K 31/506* (2006.01)
(52) U.S. Cl. ..................................................... 514/274
(58) Field of Classification Search .................. None
See application file for complete search history.

(56) References Cited

U.S. PATENT DOCUMENTS

| 4,242,363 A | 12/1980 | Lionel |
| 5,583,117 A | 12/1996 | Von Borstel et al. |
| 6,245,800 B1 * | 6/2001 | Arduini et al. ............... 514/419 |

FOREIGN PATENT DOCUMENTS

| AU | 2002-23302 A1 | 6/2002 |
| BE | 1005939 A6 * | 3/1994 |
| EP | 0348360 A2 | 12/1989 |
| IE | 913661 | 4/1992 |
| JP | 63030422 A | 2/1988 |
| WO | WO 93/13779 | 7/1993 |
| WO | WO 00/11952 | 3/2000 |
| WO | WO 02/43721 A1 | 6/2002 |

OTHER PUBLICATIONS

Chung et al.; "STATT: A Titrate-to-Goal Study of Simvastatin in Asian Patients with Coronary Heart Disease"; Jun. 2001; Clinical Therapeutics; 23(6): 858-870.*
Pirmez; BE 1005939 A6; 1994; English abstract provided by SciFinder; CAPLUS Accession No. 1994:465590.*
Meerson; "Effect of actinomycin 2703 and of stimulants of nucleic acid synthesis on development of fatigue and on physical training"; 1966; Doklady Akademii Nauk SSSR, 166(2): 496-9; English abstract: CaPlus Accession No. 1966:62441.*
Pleshakov; "Orotic acid-omega-amino acid salts for preventing fatigue during exercise"; 1983; SU 988814 A1; English abstract: CaPlus Accession No. 1983:173198.*
BE1005939; English Machine Translation provided by STIC translator.*
Abd et al.; "Statin-induced myopathy: a review and update"; 2011; Expert Opin. Drug Saf.; 10(3): 373-387.*
Pleshakov et al.; SU988814A1; 1983; English translation.*
Derwent Abstract Accession No. 94/118809/15, BE 1005939 A (1994).
Derwent Abstract Accession No. 79508X/43, DT 2462312 A (1976).
Derwent Abstract Accession No. 87-084169/12, JP 62-036322 A (1987).
Derwent Abstract Accession No. 83-813471/45, SU 988814 A (1983).
Derwent Abstract Accession No. 93-053176/32, ZA 9108336 A (1992).
Jellinek et al., "Morphological Aspects of the Effects of Orotic Acid and Magnesium Orotate on Hypercholesterolaemia in Rabbits", *Arzneimittel-Forschung (Drug Res)* 45(8):836-842 (1995).
Brown, "Cholesterol Lowering in Atherosclerosis", *Am. J. Cardiol* 86(suppl):29H-32H (2000).
Jick H. et al., "Statins and the risk of dementia", *The Lancet* 356: 1627-1631 (2000).
Blais L. et al., "3-Hydroxy-3-Methylglutaryl Coenzyme A Reductase Inhibitors and the Risk of Cancer", *Arch Intern Med.* 160: 2363-22368 (2000).
Melzack R., "The McGill Pain Questionnaire: Major Properties and Scoring Methods", *Pain 1*: 277-299 (1975).
Fisk J. D. et al., "Measuring the Functional Impact of Fatigue: Initial Validation of the Fatigue Impact Scale", *Clinical Infectious Diseases* 18(Suppl 1): S79-S83 (1994).
Robinson J.L. et al., "Assessment in Humans of Hypolipidemia Induced by Orotic Acid$^{1-3}$", *The American Journal of Clinical Nutrition* 41:605-608 (1985).
Fosslien, "Review: Mitochondrial Medicine-Molecular Pathology of Defective Oxidative Phosphorylation", *Annals of Clinical & Laboratory Science 31* (1):25-67 (2001).
Böger, "Drug Interactions of the Statins and Consequences for Drug Selection", *Int. J. Clin. Pharmacol. Ther.* 39(9):369-382 ((2001).
Geiss et al., "Effects of Magnesium Orotate on Exercise Tolerance in Patients with Coronary Heart Disease", *Cardiovascular Drugs and Therapy* 12:153-156 (1998).
Pinieux G. De et al., "Lipid-Lowering Drugs and Mitochondrial Function: Effects of HMG-CoA Reductase Inhibitors on Serum Ubiquinone and Blood Lactate/Pyruvate Ratio", *British Journal of Clinical Pharmacology* 42:333-337 (1996).
Chariot P. et al., "Simvastatin-Induced Rhabdomyolysis Followed by a Melas Syndrome", *The American Journal of Medicine* 94(1):109-110 (1993).
Walravens P.A. et al., "Lovastatin, Isoprenes, and Myopathy", *The Lancet* 334(8871):1097-1098 (1989).
http://www.medicine.ox.ac.uk/bandolier/booth/cardiac/statmusc. html, accessed Apr. 26, 2012, Bandolier, Statins and muscle, Reference: PD Thompson et al. Statin-associated myopathy, JAMA 2003 289:16811-90.
Caldwell. S. H. et al., "Myositis, Microvesicular Hepatitis, and Progression to Cirrhosis from Troglitazone Added to Simvastatin", Digestive Diseases and Sciences, 46(2):376-378 (Feb. 2001).

(Continued)

*Primary Examiner* — Timothy Thomas
(74) *Attorney, Agent, or Firm* — Scully, Scott, Murphy & Presser, P.C.

(57) ABSTRACT

The invention relates generally to treatment of muscle pain and/or fatigue and to methods of treatment of side effects of statin therapy which involve the administration of uridine, biological precursors or derivatives or uridine or salts, esters, tautomers or analogues thereof, which are collectively referred to as uridine related compounds. The invention is also directed to compositions, uses and combination packs or kits related to the treatment method.

5 Claims, No Drawings

OTHER PUBLICATIONS

Ghirlanda, G., et al., "Evidence of Plasma CoQ10-Lowering Effect by HMG-CoA Reductase Inhibitors: A Double-Blind, Placebo-Controlled Study", J Clin Pharmacol, 33:226-229 (1993).

Hamilton-Craig, I., "Statin-associated myopathy", The Medical Journal of Australia, 175(9):486-489 (Nov. 5, 2001).

Liao, J. K. et al., "Pleiotropic Effects of Statins", Annu. Rev. Pharmacol. Toxicol. 45:89-118 (2005).

Lupattelli, G. et al., "Statin induced myopathy does not show up in MIBI scintigraphy", Nuclear Medicine Communications, 22:575-578 (2001).

Marcoff, L. et al., "The Role of Coenzyme Q10 in Statin-Associated Myopathy", Journal of the American College of Cardiology, 49(23):2231-2237 (2007).

Pirmez, T., Abstract, "Medicament or food supplement providing trace elements—contg. orotic acid salt of magnesium and pref. other metals, giving rapid therapeutic effect at low dosage", 1994 Derwent Information Ltd, 94-118809/15 (May 14, 1992), 92BE-000442 (Mar. 15, 1994).

Thompson, P. D., et al., "Statin-Associated Myopathy", JAMA, 289(13):1681-1690 (Apr. 2, 2003).

* cited by examiner

TREATMENT OF STATIN SIDE EFFECTS USING URIDINE DERIVATIVES

CROSS REFERENCE TO RELATED APPLICATIONS

This application is a continuation of U.S. application Ser. No. 10/499,078 filed on Mar. 24, 2005, which is the national phase under §371 of International Application No. PCT/AU02/01685, filed on Dec. 13, 2002.

FIELD OF THE INVENTION

The present invention relates generally to treatment of muscle pain and/or fatigue and to methods for treatment of side effects of statin therapy. In particular, the invention relates to the use of uridine, biological precursors or derivatives of uridine or salts, esters, tautomers or analogues thereof ("uridine related compounds"). The invention is also directed to compositions, uses and combination packs or kits related to the treatment methods.

BACKGROUND TO THE INVENTION

There are numerous drug therapies such as AZT, corticosteroids, cancer chemotherapeutic agents and hypercholesterolemic drugs, which are known to give rise to potentially serious side effects. These effects can be disabling and may last for the duration of the causative drug treatment or even after the drug treatment is complete, affecting not only an individual's capacity to work but also perform the simple tasks involved in day to day life. One particular group of drugs for which side effects are well recognised is the statins which are commonly used to treat hypercholesterolemia, a major cause of cardiovascular disease.

Cardiovascular disease is a term that encompasses a broad range of diseases and syndromes relating to the impairment of function of the heart and its associated network of blood vessels within the body. In spite of decades of declining death rate in the developed world cardiovascular disease is still the single most common cause of death, accounting for about one third of all deaths in the United States in 1997. Cardiovascular disease has many causes and is characterised by complex interactions between the heart, blood vessels, peripheral organs and the tissues. Some types of cardiovascular disease such as coronary heart disease or stroke can occur acutely and without warning, often with severe consequences, including death. Medically these are managed with aggressive treatment (drugs and surgery) followed by chronic treatment to prevent recurrence. Other types of cardiovascular disease such as hypertension (high blood pressure) and hyperlipidemia (high cholesterol) progress slowly, often without overt symptoms, and must be managed by diet and long-term chronic drug therapy.

Although cholesterol is an essential component of a healthy functioning body, being required, amongst other things, for the formation of functional membranes, steroid hormones and bile acids, excessive levels, particularly when associated with low density lipoproteins (LDLs), constitute a health risk. It is well established that there is a cause and effect relationship between hypercholesterolemia (excessive blood cholesterol levels) and disease and mortality from coronary artery (heart) disease. Of the deaths resulting from cardiovascular disease, more than three quarters can be attributed to arteriosclerosis and more specifically to atherosclerosis and its complications.

Arteriosclerosis is a generalized disease of the arteries that develops in a symptom free manner over many years. The most common form of arteriosclerosis is atherosclerosis which often gives rise to coronary heart disease, stroke, kidney disease and peripheral vascular disease. Elevated blood cholesterol concentration is a major contributing factor in the development of atherosclerosis. In situations of excessive blood cholesterol levels, cholesterol is gradually deposited on the artery walls together with other fats, resulting in build up which disrupts the free flow of blood, with potentially severe results. To lower high cholesterol levels, patients are treated with a range of drugs, the most common class of which are the statins. The statins, examples of which include atorvastatin, simvastatin, pravastatin, lovastatin, cerivastatin, fluvastatin and crestor, are inhibitors of 3-hydroxy-3-methylglutaryl coenzyme A reductase (HMGCoA reductase). By inhibiting HMGCoA reductase and thus inhibiting the conversion of HMGCoA to mevalonate the statins act to decrease cholesterol blood/tissue levels.

The statins have also recently been reported to have potential utility in the treatment of a wide range of conditions including, but not limited to, dementia (*The Lancet*, 2000: 356; 1627-1631), various cancers, eg. prostate, skin, lung colon, bladder, uterus and kidney (*Arch. Intern. Med.* 2000, 160: 2363-2368), immune disorders, blood clotting disorders, osteoporosis, autoimmune diseases and cell cycle abnormalities.

However, there are a number of potentially serious side effects associated with statin therapy, including rhabdomyolysis, headache, joint pain, fever, muscle pain, back pain, abdominal cramping, sleep disorder, rhinitis, sinusitis, dizziness, myopathy and fatigue. Of the contraindications for this group of drugs, two of the most common are fatigue and/or muscle pain (often referred to as "myalgia"). In severe cases, these symptoms may lead to the undesirable cessation of the vital therapy. In rare cases, severe muscle wastage (rhabdomyolysis) has been reported. The risk of adverse side effects during treatment with the statins is increased with concurrent administration of certain other drugs, such as cyclosporin, fabric acid derivatives (eg. gemfibrozil), erthyromycin, niacin and antifungals. Similar symptoms to those experienced by patients undergoing statin therapy may also be experienced by patients undergoing therapy with other drugs, or may be experienced as a result of a disease state.

Thus, there exists a need for the treatment of muscle pain and fatigue generally and especially for treatment of side effects associated with certain drug therapies, particularly the side effects associated with statin therapy.

It has now been found that uridine, its biological precursors or derivatives or a salt, ester, tautomer or analogue thereof ("uridine related compounds") can usefully be administered in treating muscle pain and fatigue and for treating adverse side effects associated with some drug therapies. Uridine related compounds can therefore provide a useful adjunctive therapy to certain drug therapies.

SUMMARY OF THE INVENTION

According to one embodiment of the present invention there is provided a method of treatment of one or more side effects of statin therapy comprising administering to a subject in need of such treatment an effective amount of uridine, a biological precursor or derivative of uridine or a salt, ester, tautomer or analogue thereof.

According to another embodiment of the present invention there is provided a method of treatment of one or more side effects of statin therapy comprising administering to a subject in need of such treatment an effective amount of magnesium orotate, optionally in association with one or more pharmaceutically acceptable additives.

In a further embodiment of the present invention there is provided use of uridine, a biological precursor or derivative of uridine or a salt, ester, tautomer or analogue thereof in preparation of a medicament for treatment of one or more side effects of statin therapy.

In a still further embodiment of the invention there is provided use of magnesium orotate and optionally one or more pharmaceutically acceptable additives in preparation of a medicament for treatment of one or more side effects of statin therapy.

In another embodiment of the invention there is provided a composition comprising uridine, a biological precursor or derivative of uridine or a salt, ester, tautomer or analogue thereof in association with one or more pharmaceutically acceptable additives.

In a further embodiment of the present invention there is provided a composition comprising magnesium orotate and one or more pharmaceutically acceptable additives.

In another embodiment of the invention there is provided a composition comprising uridine, one of its biological precursors or a salt, ester, tautomer or analogue thereof and at least one statin.

In another embodiment of the invention there is provided a combination pack or kit comprising at least one statin and uridine, a biological precursor or derivative of uridine or a salt, ester, tautomer or analogue thereof wherein said pack or kit is adapted for the simultaneous, sequential or separate administration of the statin and uridine, its biological precursor or derivative or a salt, ester, tautomer or analogue thereof.

In another embodiment of the invention there is provided a combination pack or kit comprising at least one statin and magnesium orotate wherein said pack or kit is adapted for the simultaneous, sequential or separate administration of the statin and magnesium orotate.

In a further embodiment of the invention there is provided a method of treatment of muscle pain and/or fatigue comprising administering to a subject in need of such treatment an effective amount of uridine, a biological precursor or derivative of uridine or a salt, ester, tautomer or analogue thereof.

In a still further embodiment of the invention there is provided a method of treatment of a side effect of a drug therapy comprising administering to a subject in need of such treatment an effective amount of uridine, a biological precursor or derivative of uridine or a salt, ester, tautomer or analogue thereof. The drug therapy may be a therapy for hypercholesterolemia, a therapy for hyperlipidemia, a corticosteroid therapy, a therapy for chronic fatigue syndrome (CFS), a therapy for a central nervous system (CNS) disorder or a cancer chemotherapy, for example.

DETAILED DESCRIPTION OF THE INVENTION

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers.

By the phrase "uridine, a biological precursor or derivative of uridine or a salt, ester, tautomer or analogue thereof" it is intended to embrace uridine and all of those compounds which upon administration to a human or animal could be converted in vivo to uridine or derived from uridine and which have activity within the human or animal system. In vivo conversion to uridine or derivatisation from uridine may involve one or more chemical conversion steps. Clearly, this class of compounds includes a number of subclasses of uridine related compounds, including biological precursors or derivatives of uridine or salts, esters, tautomers or analogues of uridine itself or of these biological precursors or derivatives. As would be well understood by a skilled person the term "biological precursor" is intended to define compounds that would be converted over one or more steps to uridine within a human or animal system. Similarly, the term "derivative" defines compounds that in one or more steps could be derived from uridine. Preferably the conversion will be over one to four steps, preferably one or two steps. Some examples of biological precursors and derivatives of uridine include orotidine monophosphate, uridine monophosphate, uridine diphosphate, uridine triphosphate, uridine diphosphoglucose, uridine diphosphogalactose, uridine diphospoglucosamine, orotic acid, dihydroorotate, triacetyl uridine and N-carbamoylaspartate. Salts of such compounds with biologically acceptable cations such as for example ions of magnesium, sodium, calcium or potassium, as well as tautomers, such as keto-enol tautomers and esters of such compounds are also embraced by the invention. A particularly preferred salt of orotic acid is magnesium orotate.

For convenience, throughout this specification the class of compounds including uridine itself and precursors or derivatives thereof or their salts, esters or tautomers will be referred to as "uridine related compounds".

It will be appreciated that the uridine related compounds can have an asymmetric centre and therefore can exist in more than one stereoisomeric form. The invention extends to each of these forms individually and to mixtures thereof, including racemates.

Uridine or related compounds may be commercially available (eg magnesium orotate) or may be synthesised using methods known in organic chemistry, may be obtained by microbiological means or may be derived from compounds obtained by any one or more of these means.

The methods and compositions of the invention may be used to treat humans, mammals or other animal subjects. The invention is considered to be particularly suitable for the treatment of human subjects. Non-human subjects may include primates, livestock animals, domestic companion animals and laboratory test animals.

The uridine or related compounds are administered in a treatment effective amount. Reference herein to a treatment effective amount is intended to include an amount which, when administered according to a desired dosing regimen, will at least partially attain the desired therapeutic effect or will inhibit, halt or otherwise delay the onset of fatigue, muscle pain or a side effect of the drug treatment concerned. The term "treatment" therefore embraces prophylactic treatments.

Dosing may occur at intervals of hours, days or weeks and may be continued for as long as the desired therapeutic effect is maintained or required. Suitable dosages and dosing regimens can be determined by an appropriate health professional and may depend on the particular cause of the side effect, the severity of the condition as well as the general health, age and weight of the subject.

Suitable dosages of uridine related compounds lie within the range of 10 mg to 10 g per day, such as 500 mg to 5 g per day. Particularly suitable dosages lie in the range of 1000 to 4000 mg per day. Preferably the uridine related compounds are administered from once to four times per day. Some exemplary administration regimes are as follows: 1×800 mg, 1×1200 mg, 1×1600 mg or 1×2000 mg per day, or twice a day, eg 2×400 mg, 2×600 mg, 2×800 mg or 2×1000 mg. Dosage forms may be of any suitable size (eg 200 mg, 400 mg or 1000 mg). In one preferred embodiment of the invention magnesium orotate is administered twice a day as two doses each of 800 mg (which could for example comprise 2×400 mg tablets) to give a total administration of 1600 mg per day.

The methods of the invention may be used to treat any type of muscle fatigue or pain arising from certain conditions or diseases, surgery, injury or as a side effect of certain drug therapies. Muscle pain and/or fatigue associated with conditions or diseases such as chronic fatigue syndrome (CFS), fibromyalgia, myofascial pain syndrome, viral infections, myolysis, rhabdomyolysis, central nervous system (CNS) disorders such as Parkinson's disease, Alzheimer's disease, Huntington's chorea and dementia and neuromuscular diseases may also be treated by administration of uridine or related compounds.

One example of a group of therapeutic drugs characterised by side effects treatable by the present invention is the statins, of which some notable examples are atorvastatin, simvastatin, pravastatin, lovastatin, cerivastatin, creator and fluvastatin. As indicated above, common side effects associated with statin therapy include rhabdomyolysis, headache, joint pain, fever, muscle pain, back pain, abdominal cramping, sleep disorder, rhinitis, sinusitis, dizziness, myopathy, abnormal liver function and fatigue. Other examples of therapeutic drugs for which muscle fatigue and/or pain or other symptoms treatable by the inventive methods may be a side effect are AZT, hypercholesterolemia therapy drugs (apart from the statins, such as bile acid binding agents such as cholestyramine and colestipol or others such as niacin, probucol), hyperlipidemia therapy drugs such as fibric acid drugs, corticosteroids and cancer chemotherapy drugs. Other specific examples of drugs which may give rise to side effects treatable by methods of the present invention are gemfibrozil, fenofibrate, ciprofibrate, bezafibrate, betamethasone, cortisone, prednisolone, dexamethasone, hydrocortisone, methylprednisolone, adriamycin, bleomycin, dactinomycin, daunorubicin, doxorubicin, fludarabine, mitozantrone, epirubicin, tamoxifen, goserelin, carboplatin, cisplatin and etoposide or their salts, analogues or derivatives. Thus, uridine related compounds may be a useful adjunctive treatment where drugs such as the statins, or others are used to treat, for example, AIDS, hypercholesterolemia, hyperlipidemia, CFS, CNS disorders or cancers such as prostate, skin, lung, breast, colon, bladder, uterus and kidney cancers.

The uridine related compounds may be administered in conjunction (either separately, simultaneously or sequentially) with other active agents and in particular with one or more further anti-oxidant compound or compounds, such as Vitamin C or E, carotenoids or carnitine, or their derivatives or analogues.

Uridine related compounds can be administered alone or in combination with the therapeutic drug (eg a statin compound) and optionally with a further active agent or anti-oxidant. The combination of components constituting the treatment may be administered either simultaneously (as discrete dosage forms or as a single composition), sequentially, or separated by a suitable time interval. Where the components are administered as discrete dosage forms, ie not as intimate compositions, each component may be administered in the same form or a different form, eg oral, nasal, parenteral, rectal, vaginal or dermal. When the compounds are administered simultaneously, sequentially or separately, the components may be provided as discrete dosage forms. Optionally the components of the combination may be provided in a kit form wherein the kit is preferably in compartmentalised form adapted for the discrete administration of the components.

Alternatively, when the components of the combination are administered simultaneously, they may be provided as a single composition containing the two or more components or may be provided in a kit form, wherein the kit is for example compartmentalised for the simultaneous administration of the components.

Where the uridine related compound and/or anti-oxidant or other active agent, and/or the therapeutic drug are administered as discrete dosage forms, each may be formulated together with one or more pharmaceutically acceptable additives to form compositions. Where the components of the therapy are administered as a single composition, the composition may also optionally comprise one or more pharmaceutically acceptable additives.

The formulation of pharmaceutical compositions is well known to those skilled in the art. Such compositions may contain any suitable additives such as carriers, diluents or excipients, which are pharmaceutically acceptable in the sense of being compatible with the other ingredients of the composition and not injurious to the subject. Suitable additives include all conventional solvents, oils, dispersion media, fillers, solid carriers, coatings, antifungal and antibacterial agents, dermal penetration agents (where appropriate), surfactants, isotonic and absorption agents and the like. It will be understood that the compositions of the invention may also include other supplementary physiologically active agents. Further details of pharmaceutically acceptable additives may be found in Remington's Pharmaceutical Sciences, $18^{th}$ Edition, Mack Publishing Co., Easton, Pa., USA, the disclosure of which is included herein in its entirety by way of reference.

The compositions may conveniently be presented in unit dosage form and may be prepared by methods well known in the art of pharmacy. Such methods include the step of bringing into association the active ingredient with the carrier, which constitutes one or more accessory ingredients. In general, the compositions are prepared by uniformly and intimately bringing into association the active ingredient with liquid carriers or finely divided solid carriers or both, and then if necessary shaping the product.

The compounds and compositions of the invention may be presented for oral administration (although other forms such as parenteral, rectal, vaginal and dermal, may, under appropriate circumstances also be contemplated) and may be presented as discrete units such as capsules, sachets of powders or granules or tablets each containing a predetermined amount of the active ingredient; as a powder or granules; as a solution or a suspension in an aqueous or non-aqueous liquid; oils; paste; or as an oil-in-water liquid emulsion or a water-in-oil liquid emulsion. A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile.

Tablets may optionally be provided with an enteric coating, to provide release in parts of the gut other than the stomach. The compounds may also be presented in the form of hard or soft gelatin capsules It should be understood that in addition to the active ingredients particularly mentioned above, the compositions of this invention may include other agents or additives conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The compounds of the invention may also be presented for use in veterinary compositions. These may be prepared by any suitable means known in the art. Examples of such compositions include those adapted for:
  (a) oral administration, external application (eg drenches including aqueous and non-aqueous solutions or suspensions), tablets, boluses, powders, granules, pellets for admixture with feedstuffs, pastes for application to the tongue;
  (b) parenteral administration, eg subcutaneous, intramuscular or intravenous injection as a sterile solution or suspension
  (c) topical application eg creams, ointments, gels, lotions etc.

EXAMPLES

Example 1

Pilot Clinical Study

Administration of Magnesium Orotate to Patients Suffering from Statin Induced Fatigue and Muscle Pain Table 1 outlines data for seventeen patients (numbered #i-#xvii) undergoing statin therapy for treatment of hypercholesterolemia and who had reported suffering from varying levels of muscular pain and fatigue. This study is ongoing but the results below follow the study in relation to these patients for varying periods, from day 0 ($T_{0d}$) up to a maximum of 56 days ($T_{56d}$).

The design of the clinical trial involves a blood sample being taken from the patients prior to commencing medication administration and then on four further occasions during the 13 week trial, at around days 13-16, days 26-30, days 35-60 and finally at days 80-90. Patients were also required to submit answers to a questionnaire on approximately a weekly basis to enable patients to be scored for pain using the McGill Pain Questionnaire (Melzack, R., 1975 "The McGill Pain Questionnaire: Major Properties and Scoring Methods". *Pain* 1:277-299, the disclosure of which is included herein in its entirety by way of reference) scales for Pain Rating Index (PRI) and Present Pain Intensity (PPI). In the PRI index, which comprises two scores, higher scores indicate increasing levels of pain. In the PPI index present pain is given a score of 0 to 5, where 0 represents no pain and 5 represents excruciating pain. Patients were also scored prior to commencement of the trial medication for fatigue using the Fatigue Impact Scale (Fisk, J. D. et al, 1994, "Measuring the functional impact of fatigue: Initial Validation of the Fatigue Impact Scale", *Clinical Infectious Disease,* 18 (Suppl 1):S79-83, the disclosure of which is included herein in its entirety by way of reference). On the first week at the clinic, prior to commencement of the trial medication, details of the patients' statin medication were recorded and daily doses noted.

After the pre-trial medication blood samples and questionnaires were taken ($T_{0d}$) patients commenced taking daily doses of 1600 mg of magnesium orotate, administered as 2×400 mg tablets, morning and evening.

Blood samples were taken prior to commencement of trial medication ($T_{0d}$) and after approximately 14 ($T_{14d}$), 28 ($T_{28d}$), 42 ($T_{42d}$) and 56 ($T_{56d}$) days to determine individual to baseline levels of uridine (µg/ml) arising from magnesium orotate (MgOr) administration, to thereby monitor patient compliance. Blood samples taken were also used to determine creatine kinase concentration (CK) (units/L), gamma glutaryl transferase (GGT) concentration, aspartate amino transferase (AST) concentration and alanine aminotransferase concentration (ALT) (units/L), as well as serum lipid levels including total cholesterol concentration, high density lipoprotein (HDL-CHOL) concentration, low density lipoprotein (LDL-CHOL) concentration, tryglyceride (TRIG) concentration and levels of other serum components routinely tested for including magnesium ion concentration. Table 1 shows the normal parameters of blood serum components that are routinely monitored, for both males and females.

As can be seen from the results shown in Table 2 significant improvements in PRI and PPI pain scores and FIS fatigue score were recorded in most patients undergoing the magnesium orotate therapy, which demonstrates activity in treating pain and fatigue.

A preliminary statistical analysis of the results of the PRI, PPI and FIS tests for the patients on the trial as a group are presented in Table 3, below. Importantly the P values obtained using a paired T test demonstrate statistical significance for reduction of pain according to both the PRI and PPI rating scales as well as for reduction of fatigue, at each of $T_{7d}$, $T_{14d}$, $T_{21d}$ and $T_n$ (where $T_n$ represents the combined results at the last available time point for each of the patients on the trial).

Although the data is not presented, monitoring generally of serum uridine concentration has identified an increase in serum uridine concentration for all patients on the trial, which indicates the patients are complying with the trial magnesium orotate administration regime. Monitoring of other serum components has demonstrated across the board that there has been no significant alteration during the course of the trial in total cholesterol concentration, high density lipoprotein (HDL-CHOL) concentration, low density lipoprotein (LDL-CHOL) concentration, tryglyceride (TRIG) concentration or magnesium ion concentration (magnesium).

In relation to the monitoring of serum components indicative of liver function, including gamma glutaryl transferase (GGT), alanine amino transferase (ALT) and aspartate amino transferase (AST), there was no significant impact in the serum concentration levels during the course of the study in respect of all of those patients who were generally within the normal ranges for these components at commencement of the trial. Interestingly, in relation to the only patient who was significantly outside the normal range in respect of each of GGT, ALT and AST serum levels at commencement of the trial, these levels dropped quite significantly during the course of the study. For this patient the GGT serum concentration dropped from 96 U/L at day 0 to 83 U/L at day 43, ALT serum concentration dropped from 105 U/L at commencement to 74 U/L at day 43 and AST serum concentration dropped from 56 U/L at commencement to 42 U/L, at day 43.

Similarly, in relation to the monitoring of serum creatine kinase concentration (CK), which is an indicator of muscular damage, there was no significant impact in concentration levels during the course of the study in respect of those patients who were generally within the normal ranges for these components at commencement of the trial. However, an adjustment towards the normal range was observed in relation to three patients who had serum CK levels significantly above the normal at commencement of the study. For these three male patients the CK serum concentration dropped respectively from 398 U/L to 378 U/L, from 253 U/L to 185 U/L and from 395 U/L to 292 U/L during the time they have participated in the trial.

Those skilled in the art will appreciate that the invention described herein is susceptible to variations and modifications other than those specifically described. It is to be understood that the invention includes all such variations and modifications which fall within the spirit and scope of this general description. The invention also includes all of the steps, features, compositions and compounds referred to or indicated in this specification, individually or collectively, and any and all combinations of any two or more of said steps or features.

TABLE 1

| SERUM COMPONENT | FEMALE | | MALE | |
|---|---|---|---|---|
| | Units | Range | Units | Range |
| S T-BILI | μmol/L | (2-20) | μmol/L | (2-20) |
| S ALP | U/L | (20-120) | U/L | (30-120) |
| S GGT | U/L | (5-45) | U/L | (5-65) |
| S ALT | U/L | (5-40) | U/L | (5-40) |
| S AST | U/L | (5-40) | U/L | (5-40) |
| S T PROTEIN | g/L | (60-80) | g/L | (60-80) |
| S ABLUMIN | g/L | (35-50) | g/L | (35-50) |
| S GLOBULIN | g/L | (20-36) | g/L | (20-36) |
| S MAGNESIUM | mmol/L | (0.65-1.30) | mmol/L | (0.65-1.30) |
| S CK | U/L | (25-150) | U/L | (40-200) |
| S CHOLESTEROL | mmol/L | (3.5-5.5) | mmol/L | (3.5-5.5) |
| S TRIG | mmol/L | (0.5-2.0) | mmol/L | (0.5-2.0) |
| S HDL-CHOL | mmol/L | (>1.20) | mmol/L | (>1.00) |
| S LDL-CHOL | mmol/L | (<3.5) | mmol/L | (<3.5) |
| S LDL:HDL Ra | | (<4.0) | | (<4.0) |
| P GLU (AM) | mmol/L | (3.6-7.7) | mmol/L | (3.6-7.7) |

TABLE 2

| Patient Number | Statin* & Dose | PRI—Pain Rating Index Time (Days) | | | | | | | | | PPI—Present Pain Intensity | | | | | | | | |
|---|---|---|---|---|---|---|---|---|---|---|---|---|---|---|---|---|---|---|---|
| | | $T_{0d}$ | $T_{7d}$ | $T_{14d}$ | $T_{21d}$ | $T_{28d}$ | $T_{35d}$ | $T_{42d}$ | $T_{49d}$ | $T_{56d}$ | $T_{0d}$ | $T_{7d}$ | $T_{14d}$ | $T_{21d}$ | $T_{28d}$ | $T_{35d}$ | $T_{42d}$ | $T_{49d}$ | $T_{56d}$ |
| SUH 001 | L-80 mg | 8 | 3 | 3 | 0 | 0 | 0 | 0 | 0 | 0 | 2 | 0 | 1 | 0 | 0 | 0 | 0 | 0 | 0 |
| SUH 003 | P-20 mg | 82 | 0 | 0 | 3 | 2 | 0 | 0 | | | 2 | 0 | 1 | 1 | 2 | 0 | 0 | | |
| SUH 008 | L-40 mg | 16 | 7 | — | 12 | | | | | | 2 | 1 | — | 1 | | | | | |
| SUH 009 | P-40 mg | 16 | 16 | 6 | 8 | | | | | | 2 | 0 | 1 | 1 | | | | | |
| SUH 010 | L-50 mg | 15 | 14 | 9 | 9 | 2 | | | | | 2 | 2 | 2 | 2 | 1 | | | | |
| SUH 011 | Z-40 mg | 21 | 5 | 8 | 8 | 3 | | | | | 2 | 2 | 1 | 1 | 0 | | | | |
| SUH 012 | Z-20 mg | 32 | 21 | 28 | 24 | | | | | | 2 | 1 | 1 | 1 | | | | | |
| SUH 013 | L-20 mg | 37 | 10 | 16 | 13 | 11 | | | | | 2 | 1 | 2 | 1 | 1 | | | | |
| SUH 014 | L-20 mg | 30 | 23 | 23 | 15 | 4 | | | | | 2 | 2 | 2 | 2 | 1 | | | | |
| SUH 015 | P-40 mg | 48 | 22 | 42 | 42 | 3 | | | | | 2 | 1 | 2 | 2 | 0 | | | | |
| SUH 016 | L-10 mg | 12 | 7 | 4 | 2 | 2 | | | | | 2 | 1 | 1 | 1 | 1 | | | | |
| SUH 017 | Z-40 mg | 11 | 29 | 7 | | | | | | | 1 | 1 | 1 | | | | | | |
| SUH 018 | L-20 mg | 61 | 16 | 15 | — | | | | | | 3 | 1 | 1 | — | | | | | |
| SUH 020 | L-15 mg | 16 | 17 | 37 | 35 | | | | | | 2 | 2 | 2 | 2 | | | | | |
| SUH 022 | L-20 mg | 13 | 12 | — | 9 | | | | | | 1 | 1 | — | 2 | | | | | |
| SUH 023 | Z-80 mg | 27 | — | 9 | | | | | | | 2 | — | 2 | | | | | | |
| SUH 024 | Z-20 mg | 18 | 2 | 2 | | | | | | | 2 | 1 | 1 | | | | | | |

| Patient Number | FIS—Fatigue Impact Scale Time (Days) | | | | | | | | |
|---|---|---|---|---|---|---|---|---|---|
| | $T_{0d}$ | $T_{7d}$ | $T_{14d}$ | $T_{21d}$ | $T_{28d}$ | $T_{35d}$ | $T_{42d}$ | $T_{49d}$ | $T_{56d}$ |
| SUH 001 | 4 | 0 | 0 | 0 | 0 | 0 | 0 | 0 | 0 |
| SUH 003 | 100 | 19 | 38 | 19 | 22 | 22 | 13 | | |
| SUH 008 | 37 | 9 | — | 18 | | | | | |
| SUH 009 | 59 | 23 | 25 | 39 | | | | | |
| SUH 010 | 102 | 88 | 86 | 92 | 51 | | | | |
| SUH 011 | 29 | 7 | 9 | 4 | 1 | | | | |
| SUH 012 | 31 | 24 | 32 | 30 | | | | | |
| SUH 013 | 39 | 17 | 9 | 8 | 7 | | | | |
| SUH 014 | 101 | 101 | 86 | 91 | 77 | | | | |
| SUH 015 | 7 | 5 | 9 | 10 | 9 | | | | |
| SUH 016 | 48 | 47 | 49 | 67 | 50 | | | | |
| SUH 017 | 66 | 77 | 3 | | | | | | |
| SUH 018 | 76 | 44 | 48 | — | | | | | |
| SUH 020 | 32 | 40 | 31 | 21 | | | | | |
| SUH 022 | 9 | 6 | — | 3 | | | | | |
| SUH 023 | 18 | — | 11 | | | | | | |
| SUH 024 | 14 | 21 | 21 | | | | | | |

Statin*
L—Liptor
P—Pravachol
Z—Zocor

TABLE 3

| Paired T-Test | PRI | | | | PPI | | | | FIS | | | |
|---|---|---|---|---|---|---|---|---|---|---|---|---|
| | $T_{d7}$ | $T_{d14}$ | $T_{d21}$ | $T_n$ | $T_{d7}$ | $T_{d14}$ | $T_{d21}$ | $T_n$ | $T_{d7}$ | $T_{d14}$ | $T_{d21}$ | $T_n$ |
| Number of patients (n) | 16 | 15 | 13 | 17 | 16 | 15 | 13 | 17 | 16 | 15 | 13 | 17 |
| P values | .023 | .025 | .059 | .004 | .001 | .003 | .014 | .001 | .027 | .007 | .040 | .003 |

The invention claimed is:

1. A method of treatment of muscle pain side effects of statin therapy comprising identifying a human subject who is undergoing statin therapy and suffers from said muscle pain statin side effects, and administering to said subject an effective amount of uridine, a biological precursor thereof that is converted to uridine in vivo over one, two, three or four steps or a salt thereof, wherein the salt is selected from a magnesium, sodium, calcium or potassium salt.

2. The method according to claim 1 wherein the biological precursor of uridine is orotic acid or a salt thereof, wherein the salt is selected from a magnesium, sodium, calcium or potassium salt.

3. The method according to claim 1 wherein the salt of a biological precursor of uridine is magnesium orotate.

4. A method of treatment of muscle pain side effects of statin therapy comprising identifying a human subject who is undergoing statin therapy and suffers from said muscle pain statin side effects, and administering to said subject an effective amount of magnesium orotate in association with one of more pharmaceutically acceptable additives.

5. The method of claim 3 or claim 4, wherein magnesium orotate is administered at 1600 mg per day to said patient.

* * * * *